(12) United States Patent
Coleman et al.

(10) Patent No.: US 7,144,697 B1
(45) Date of Patent: Dec. 5, 2006

(54) SYNTHETIC ANTIGEN FOR THE DETECTION OF ANTIBODIES IMMUNOREACTIVE WITH HIV VIRUS

(75) Inventors: Patrick F. Coleman, Edmonds, WA (US); Peter Chong-Dug Su, Mercer Island, WA (US); Nobuo Monji, Seattle, WA (US); Carol-Ann Cole, Seattle, WA (US)

(73) Assignee: Bio-Rad Laboratories, Hercules, CA (US)

( * ) Notice: Subject to any disclaimer, the term of this patent is extended or adjusted under 35 U.S.C. 154(b) by 0 days.

(21) Appl. No.: 09/515,014

(22) Filed: Feb. 29, 2000

Related U.S. Application Data

(63) Continuation of application No. 08/904,826, filed on Aug. 1, 1997, now abandoned.

(51) Int. Cl.
*C12Q 1/70* (2006.01)
(52) U.S. Cl. ............................................. 435/5
(58) Field of Classification Search ............... 435/5, 435/7.92–7.95; 530/324–330, 350, 388, 530/35; 536/23.72
See application file for complete search history.

(56) References Cited

U.S. PATENT DOCUMENTS

| 4,629,783 | A |   | 12/1986 | Cosand ...................... 530/324 |
| 5,075,211 | A | * | 12/1991 | Cosand et al. ................. 435/5 |
| 5,206,136 | A |   | 4/1993  | Monji et al. ................... 435/5 |
| 5,221,610 | A | * | 6/1993  | Montagnier et al. ......... 435/7.1 |
| 5,439,792 | A |   | 8/1995  | Blake et al. ................... 435/5 |
| 5,858,646 | A | * | 1/1999  | Kang ............................ 435/5 |

FOREIGN PATENT DOCUMENTS

| EP | 0 267 802       |   | 3/1998 |
| RU | 2043411 C1      | * | 9/1995 |
| RU | 2085586 C1      | * | 7/1997 |
| WO | 83/02277        |   | 7/1983 |

OTHER PUBLICATIONS

Choi, W.S. "Effects of Natural Sequence Variation on Recognition by Monoclonal Antibodies That Neutralize Simian Immunodeficiency Virus" J. Virol. (Sep. 1994) 68, 9, 5395-5402.*
Berent et al., "Comparison of Oligonucleotide and Long DNA Fragments as Probes in DNA and RNA Dot, Southern, Northern, Colony and Plaque Hybridizations," *Biotechniques* 3(3):208-219 (1985).
Clavel et al., "Isolation of a New Human Retrovirus from West African Patients with AIDS," *Science* 233(4761):343-346 (1986).
De Leys et al., "Isolation and Partial Characterization of an Unusual Human Immunodeficiency Retrovirus from Two Persons of West-Central African Origin," *J. Virol* 64(3):1207-1216 (1990).
Gürtler et al., "A New Subtype of Human Immunodeficiency Virus Type 1 (MVP-5180) from Cameroon," *J. Virol.* 68(3):1581-1585 (1994).
Guyader et al., "Genome organization and transactivation of the human immunodeficiency virus type 2," *Nature* 326:662-669 (1987).
Ratner et al., "Complete nucleotide sequence of the AIDS virus, HTLV-III," *Nature* 313:277-284 (1985).
Tam et al., "$S_N2$ Deprotection of Synthetic Peptides with a Low Concentration of HF in Dimethyl Sulfide: Evidence and Application in Peptide Synthesis," *Am. Chem. Soc.* 1056442-6455 (1983).
Hickman et al., "Detection and Differentiation of HIV-1 group O sera from HIV-1 Group M and HIV-2 Using Recombinant Antigens and Peptides," *J. Virol. Meth.* 72:43-49 (1998).
Monji N. et al., "Sensitive and Specific Hiv-1/HIV-2 EIA Using Env and Pol Synthetic Peptdies," *Biosis* Database Accession No. PREV199698616393 XP001105703 (1995).
Monji Nobuo et al., "Specific and Sensitive HIV-1/HIV-2 EIA Using Env and Pol Synthetic Peptides," *Biosis* Database Accession No. PREV199598347548 XP001105443 (1995).
Ivanov V. et al., "Study of the Antigenic Structure of Human Immunodeficiency Viruses by Means of Synthetic Peptides," *Biosis* Database Accession No. PREV199294121790, X002213768 (1992).
D.E. Pollet et al., "Confirmation and Differentiation of Antibodies to Human Immunodeficiency Virus 1 and 2 with a Strip-Based Assay Including Recombinant Antigens and Synthetic Peptides" *Clin. Chem.* 37 1700-1707 (1991).
Sprengers et al., "A MicroELISA System for the Detection of Both Anti-HIV-1 and Anti-HIV-2Antibodies," *J. Immunol. Meth.* 139:77-82 (1991).
Wain-Hobson et al., "Nucleotide Sequence of the Aids Virus, LAV," *Cell* 10:9-17 (1988).
Sternberg et al., "Prediction of Antigenic Determinants and Secondary Structures of the Major AIDS Virus Proteins," *FEBS Lett.* 218 P231-237 (1987).

* cited by examiner

*Primary Examiner*—Mary E. Mosher
(74) *Attorney, Agent, or Firm*—Townsend & Townsend & Crew LLP

(57) ABSTRACT

Novel polypeptides are provided having substantially the same sequence as immunologically significant fragments of AIDS-related viruses. The polypeptides can be used as reagents in the determination of exposure of a human host to the virus. Of particular interest is the use of polypeptides in screening blood products.

11 Claims, No Drawings

```
                              SEQUENCE LISTING

<160> NUMBER OF SEQ ID NOS: 11

<210> SEQ ID NO 1
   <211> LENGTH: 30
   <212> TYPE: PRT
   <213> ORGANISM: Human immunodeficiency virus type 1

<400> SEQUENCE: 1

Lys Ile Gln Asn Phe Arg Val Tyr Tyr Arg Asp Ser Arg Asp Pro Leu
    1               5                  10                  15

Trp Lys Gly Pro Ala Lys Leu Leu Trp Lys Gly Glu Gly Ala
               20                  25                  30

<210> SEQ ID NO 2
   <211> LENGTH: 36
   <212> TYPE: PRT
   <213> ORGANISM: Human immunodeficiency virus type 1

<400> SEQUENCE: 2

Leu Gln Lys Gln Ile Thr Lys Ile Gln Asn Phe Arg Val Tyr Tyr Arg
    1               5                  10                  15

Asp Ser Arg Asp Pro Leu Trp Lys Gly Pro Ala Lys Leu Leu Trp Lys
               20                  25                  30

Gly Glu Gly Ala
           35

<210> SEQ ID NO 3
   <211> LENGTH: 40
   <212> TYPE: PRT
   <213> ORGANISM: Human immunodeficiency virus type 1

<400> SEQUENCE: 3

Lys Ile Gln Asn Phe Arg Val Tyr Tyr Arg Asp Ser Arg Asp Pro Leu
    1               5                  10                  15

Trp Lys Gly Pro Ala Lys Leu Leu Trp Lys Gly Glu Gly Ala Val Val
               20                  25                  30

Ile Gln Asp Asn Ser Asp Ile Lys
           35                  40

<210> SEQ ID NO 4
   <211> LENGTH: 36
   <212> TYPE: PRT
   <213> ORGANISM: Human immunodeficiency virus type 1

<400> SEQUENCE: 4

Lys Ile Gln Asn Phe Arg Val Tyr Tyr Arg Asp Ser Arg Asp Pro Leu
    1               5                  10                  15

Trp Lys Gly Pro Ala Lys Leu Leu Trp Lys Gly Glu Gly Ala Val Val
               20                  25                  30

Ile Gln Asp Asn
           35
```

```
<210> SEQ ID NO 5
<211> LENGTH: 30
<212> TYPE: PRT
<213> ORGANISM: Human immunodeficiency virus type 2

<400> SEQUENCE: 5

Lys Leu Lys Asp Phe Arg Val Tyr Phe Arg Glu Gly Arg Asp Gln Leu
  1               5                  10                  15

Trp Lys Gly Pro Gly Glu Leu Leu Trp Lys Gly Glu Gly Ala
            20                  25                  30

<210> SEQ ID NO 6
<211> LENGTH: 36
<212> TYPE: PRT
<213> ORGANISM: Human immunodeficiency virus type 2

<400> SEQUENCE: 6

Leu Gln Ala Lys Asn Ser Lys Leu Lys Asp Phe Arg Val Tyr Phe Arg
  1               5                  10                  15

Glu Gly Arg Asp Gln Leu Trp Lys Gly Pro Gly Glu Leu Leu Trp Lys
            20                  25                  30

Gly Glu Gly Ala
        35

<210> SEQ ID NO 7
<211> LENGTH: 40
<212> TYPE: PRT
<213> ORGANISM: Human immunodeficiency virus type 2

<400> SEQUENCE: 7

Lys Leu Lys Asp Phe Arg Val Tyr Phe Arg Glu Gly Arg Asp Gln Leu
  1               5                  10                  15

Trp Lys Gly Pro Gly Glu Leu Leu Trp Lys Gly Glu Gly Ala Val Leu
            20                  25                  30

Val Lys Val Gly Thr Asp Ile Lys
        35                  40

<210> SEQ ID NO 8
<211> LENGTH: 33
<212> TYPE: PRT
<213> ORGANISM: Human immunodeficiency virus type 2

<400> SEQUENCE: 8

Tyr Phe Arg Glu Gly Arg Asp Gln Leu Trp Lys Gly Pro Gly Glu Leu
  1               5                  10                  15

Leu Trp Lys Gly Glu Gly Ala Val Leu Val Lys Val Gly Thr Asp Ile
            20                  25                  30

Lys

<210> SEQ ID NO 9
<211> LENGTH: 40
<212> TYPE: PRT
<213> ORGANISM: Human immunodeficiency virus type 2

<400> SEQUENCE: 9

Lys Leu Lys Asp Phe Arg Val Tyr Phe Arg Glu Gly Arg Asp Gln Leu
  1               5                  10                  15

Trp Lys Gly Pro Gly Glu Leu Leu Trp Lys Gly Glu Gly Ala Val Leu
            20                  25                  30

Val Lys Val Gly Thr Asp Ile Lys
        35                  40
```

```
<210> SEQ ID NO 10
<211> LENGTH: 33
<212> TYPE: PRT
<213> ORGANISM: Human immunodeficiency virus type 2

<400> SEQUENCE: 10

Lys Gly Pro Gly Glu Leu Leu Trp Lys Gly Glu Gly Ala Val Leu Val
 1               5                  10                  15

Lys Val Gly Thr Asp Ile Lys Ile Ile Pro Arg Arg Lys Ala Lys Ile
            20                  25                  30

Ile

<210> SEQ ID NO 11
<211> LENGTH: 36
<212> TYPE: PRT
<213> ORGANISM: Human immunodeficiency virus type 2

<400> SEQUENCE: 11

Lys Leu Lys Asp Phe Arg Val Tyr Phe Arg Glu Gly Arg Asp Gln Leu
 1               5                  10                  15

Trp Lys Gly Pro Gly Glu Leu Leu Trp Lys Gly Glu Gly Ala Val Leu
            20                  25                  30

Val Lys Val Gly
            35
```

SYNTHETIC ANTIGEN FOR THE DETECTION OF ANTIBODIES IMMUNOREACTIVE WITH HIV VIRUS

RELATED APPLICATIONS

This application is a continuation of U.S. Ser. No. 08/904,826; filed on Aug. 1, 1997 (now abandoned), the disclosure of which is incorporated herein by reference in its entirety.

FIELD OF THE INVENTION

This invention relates to synthetic polypeptides useful for detecting antibodies associated with human immunodeficiency virus type 1 (HIV-1) and/or type 2 (HIV-2) (as used herein, "HIV" used without reference to the type shall mean either or both types), and particularly relates to synthetic polypeptides which mimic antigenic epitopes of the gene products of the HIV polymerase region.

BACKGROUND OF THE INVENTION

Human immunodeficiency virus type 1 and 2 (HIV-1 and HIV-2) are known to cause acquired immune deficiency syndrome (AIDS). Both viruses apparently exhibit similar modes of transmission. HIV-1 and HIV-2 were both isolated in the early 1980's from African AIDS patients. Since then, cases have been found in most countries of the world. Because the HIV viruses exhibit rapid genetic drift, widely divergent strains are emerging. Detection and treatment of variant strains has proven to be challenging and difficult.

Individuals with antibodies reactive with HIV-1 and/or HIV-2 are determined by immunoassays of the conventional sandwich ELISA format. These assays are comprised of an immobilized viral antigen, that may be comprised of viral lysate, retrovirus proteins or natural or synthetic polypeptides, that is contacted with blood or serum components suspected of containing HIV antibodies. While the existing commercial tests appear to have significantly diminished the transmission of HIV virus in blood products, each test configuration may have some disadvantages.

The possible disadvantages of viral lysate tests include: the need to grow and handle large quantities of live infectious virus; the possibility that the live virus might be incorporated into test materials; the variable nature of the resulting viral lysate; and the substantial number of false positive and false negative results that require additional confirmatory testing. These disadvantages may also be associated with the use of isolated viral proteins as antigens.

The use of synthetic polypeptides, which can be engineered to immunologically mimic antigenic epitopes of the HIV viruses, may avoid some of the above-mentioned disadvantages. One area of concern with the use of synthetic polypeptides (less than or equal to 60 residues in length) in diagnostic assays is the consideration that viral antigenic drift could result in the failure to detect HIV-1 or HIV-2 infected sera using these assays, presumably due to the limited presentation of viral epitopes. One method of guarding against such an occurrence is to include polypeptides from different immunodominant regions of the viral genome. Thus, synthetic polypeptides that immunologically mimic immunodominant regions of the HIV-1 and HIV-2 pol gene products are important additions to the already described polypeptides that mimic the env, gag, and pol proteins of HIV-1 and HIV-2. U.S. Pat. Nos. 4,629,783 and 5,075,211 describe synthetic polypeptides that mimic antigenic determinants of HIV-1. Cosand U.S. Pat. No. 5,075,211 describes synthetic polypeptides that immunologically mimic antigenic epitopes of HIV-1 proteins from the pol region, including two polypeptides which are similar to the polypeptides of this invention. In blood screening assays, the greater the immunoreactivity of the antigens used in the assay method, the less likely antibodies to a new variant or subtype of HIV-1 or HIV-2, present in a patient's sample, will be left undetected.

U.S. Pat. No. 5,306,466 describes an "HIV-3 retrovirus" which was initially believed to be separate and distinct from HIV-1 and HIV-2. Researchers have since determined that the HIV-3 retrovirus is merely a particular subtype of HIV-1, now referred to as subtype O, or Group O. [R. De Leys, et. al., J. Virol.: 1207–1216 (1990); L. G Gürtler, et. al., J. Virol.:1581–1585 (1994)]

By comparing various HIV-1 isolates researchers have shown that some regions of the genome are highly variable while others are reasonably well conserved. Similar polymorphisms have also been observed for HIV-2.

Despite the apparent similarities in disease state and transmission of HIV-1 and HIV-2 viruses, the virus types have been differentiated based on their genetic divergence. Based on genetic analysis viral isolates can be grouped according to their genetic homology to previous isolates. Today, HIV-1 and HIV-2 form the two main branches of the HIV genetic tree. DNA hybridization studies suggest that, while regions of extensive homology exist between HIV-1 and HIV-2, other regions seem very divergent. (Clavel et al, Science 233: 343 (1986)). In fact, HIV-2 has been shown to have overall, only about 40% homology with HIV-1, and studies have shown little immunological cross reactivity between the envelope glycoproteins. The limited serologic cross reactivity between these viruses makes screening assays based on HIV-1 antigens insufficient for screening or diagnosis of HIV-2 infection in human sera.

SUMMARY OF THE INVENTION

Polypeptide sequences capable of mimicking immunodominant regions of HIV-1 or HIV-2 proteins, encoded in the polymerase region, have been identified. These synthetic polypeptides are useful in the preparation of reagents for the screening of blood and blood products for exposure to HIV viruses. The polypeptides can be used in various specific binding assays for the detection of antibodies to HIV-1 and/or HIV-2 virus, for the detection of HIV-1 and/or HIV-2 antigens, or as immunogens in vaccine compositions.

DETAILED DESCRIPTION OF THE SPECIFIC EMBODIMENTS

Novel polypeptides are provided that immunologically mimic proteins encoded by the HIV-1 or HIV-2 retroviruses, respectively, particularly proteins encoded in the polymerase region of the viral genome. Each polypeptide of the invention may be modified by introducing conservative or non-conservative substitutions into the polypeptide, usually fewer than 20 number percent, and more usually fewer than 10 number percent of the amino acids being exchanged. In those situations where regions are found to be structurally polymorphic, it may be desirable to vary one or more particular amino acid to more effectively mimic the differing epitopes of the different retroviral strains. In many instances to provide chemical stability, methionine may be replaced by norleucine (Nor).

One particularly useful means of choosing appropriate amino acid substitutions in a polypeptide of the invention would be a substitution which occurs naturally in one or more isolate of the virus.

In general, the term "polypeptide" or "peptide" used herein shall mean a chain of amino acid molecules possessing biological activity. The terms do not relate to a product of any specific length.

It should be understood that the polypeptide employed in the subject invention need not be identical to any particular HIV-1 or HIV-2 polypeptide sequence, so long as the subject compound is able to immunologically mimic an epitope of the pol region of at least one of the strains of the HIV-1 or HIV-2 retrovirus. Therefore, the subject polypeptide may be modified to include various changes, as mentioned above, such as insertions, deletions, and substitutions, either conservative or non-conservative, where such changes might provide for certain advantages in their use. By conservative substitutions is intended substitutions within groups such as gly, ala; val, ile, leu; asp, glu; asn, gin; ser, thr; lys, arg; phe, tyr; and nor, met. Usually, the sequence will not differ by more than 20% from the sequence of at least one strain of an HIV-1 or HIV-2 retrovirus except where additional amino acids may be added at either terminus for the purpose of providing an "arm" by which the polypeptide of this invention may be conveniently immobilized. The arms will usually be at least 1 amino acid and may be 50 or more amino acids, more often 1 to 10 amino acids, in length. A polypeptide in which the amino acid sequence is modified by the substitution, addition, or deletion of amino acid residues should retain substantially all of the immunological reactivity of the unmodified polypeptide, which may be conveniently measured by radioimmuno-precipitation, immunofluorescence, or enzyme-linked immunosorbant assays.

In addition, one or two amino acids may be added to the termini of an oligopeptide or polypeptide to provide for ease of linking polypeptides one to another, for coupling to a support or larger polypeptide, for reasons to be discussed subsequently, for modifying the physical or chemical properties of the polypeptide or oligopeptide, or the like.

Amino acids such as tyrosine, cysteine, lysine, glutamic or aspartic acid, or the like, may be introduced at the C- or N-terminus of the polypeptide to provide for a useful functionality for linking. Cysteine is particularly preferred to facilitate covalent coupling to other polypeptides or, for example, to form dimers by oxidation. To form polymers, it is preferred to have at least two cysteine residues present in the molecules being linked, preferably by utilizing cysteine residues added to the terminal portions of the polypeptides. Combinations of cysteine with intervening amino acid spacers are also useful. For example, two cysteine residues can be separated by one or more amino acid residue. Glycine residues are particularly useful and from one to three glycine residues may be employed between amino acids.

In addition, the subject polypeptide sequences may differ from the natural sequence after being modified by terminal-$NH_2$ acylation, e.g. acetylation, or thioglycolic acid amidation, terminal-carboxy amidation, e.g. with ammonia or methylamine, to provide stability, increased hydrophobicity for linking or binding to a support or other molecule, or for polymerization.

The polypeptides of the invention, derived from the polymerase region of HIV-1 are described below. The family of HIV-1 polypeptides are encoded by the genomic nucleotide sequences (LAI or BRU isolate) encompassing base pairs (bp) 4448 through (bp) 4585 (numbering of Genbank HIVBRUCG; Accession K02013, BRU isolate) or is encoded in the pol open reading frame from about amino acid residue numbers 940 to about 985.

Polypeptide I has the following polypeptide sequence:

(I) BRU124E

W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

Another polypeptide of the invention, Polypeptide II, also designated BRU124EX, has the following polypeptide sequence:

(II) BRU124EX

W-X-Leu-Gln-Lys-Gln-Ile-Thr-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

Another polypeptide of the invention, Polypeptide III, also designated BRU124F1X, has the following polypeptide sequence:

(III) BRU124F1X

W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Val-Val-Ile-Gln-Asp-Asn-Ser-Asp-Ile-Lys-Y-Z

Another polypeptide of the invention, Polypeptide IV, also designated BRU124F3X, has the following polypeptide sequence:

(IV) BRU124F3X

W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Val-Val-Ile-Gln-Asp-Asn-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

The polypeptides of the invention, derived from the polymerase region of HIV-2 are described below. Polypeptide V, also designated ROD124E1, is encoded by the nucleotide sequence of the HIV-2 genome encompassing base pairs (bp) 4694 through (bp) 4861 (numbering by Genbank HIV2ROD; Accession M15390, HIV-2ROD isolate) or is encoded in the pol open reading frame from about amino acid residue numbers 956 through 1001.

Polypeptide V has the following polypeptide sequence:

(V) ROD124E1

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

Another polypeptide of the invention, Polypeptide VI, also designated ROD 124EX, has the following polypeptide sequence:

(VI) ROD 124EX

W-X-Leu-Gln-Ala-Lys-Asn-Ser-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly-; Y is absent or Cys; and Z is OH or $NH_2$.

Another polypeptide of the invention, Polypeptide VII, also designated ROD 124C2X, has the following polypeptide sequence:

(VII) ROD 124C2X

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr- Asp-Ile-Lys-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly-; Y is absent or Cys; and Z is OH or $NH_2$.

Another polypeptide of the invention, Polypeptide VIII, also designated ROD 124C1X, has the following polypeptide sequence:

(VIII) ROD 124C1X

W-X-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly-; Y is absent or Cys; and Z is OH or $NH_2$.

Another polypeptide of the invention, Polypeptide IX, also designated ROD123 C3X, has the following polypeptide sequence:

(IX) ROD123C3X

X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Y-Z wherein X is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; Y is absent or Cys; and Z is OH or $NH_2$.

Another polypeptide of the invention, Polypeptide X, also designated POL2A1, has the following polypeptide sequence:

(X) POL2A1

W-X-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Ile-Ile-Pro-Arg-Arg-Lys-Ala-Lys-Ile-Ile-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

Another polypeptide of the invention, Polypeptide XI, also designated ROD124C5X, has the following polypeptide sequence:

(XI) ROD124C5X

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Y-Z wherein W is either a H of the amino terminal $NH_2$ group of the polypeptide or an additional amino acid bonded to the amino terminal $NH_2$ group of the polypeptide, the additional amino acid being selected to facilitate coupling of the polypeptide to a carrier protein or to a support; X is absent or Cys-Gly-Gly; Y is absent or Cys; and Z is OH or $NH_2$.

Of particular interest is the use of the mercaptan group of cysteines or thioglycolic acids used for acylating terminal amino groups or the like for linking two of the polypeptides or oligopeptides or combinations thereof by a disulfide linkage or a longer linkage. To achieve this, compounds may be employed having bis-haloacetyl groups, nitroarylhalides, or the like where the reagents are specific for thio groups. Thus, the linking between the two mercapto groups of the different polypeptides or oligopeptides may be a single bond or a linking group of at least 2, usually at least 4, and not more than about 16, usually not more than about 14 carbon atoms.

The subject polypeptides may be employed linked to a soluble macromolecular (e.g., not less than 5 kDal) carrier. Conveniently, the carrier may be a poly(amino acid), either naturally occurring or synthetic, to which antibodies are unlikely to be encountered in human serum. Illustrative polypeptides include poly-L-lysine, bovine serum albumin, keyhole limpet hemocyanin, bovine gamma globulin, etc. The choice is primarily one of convenience and availability.

With such conjugates, there will be at least one molecule of at least one subject polypeptide per macromolecule and not more than about 1 per 0.5 kDal, usually not more than about 1 per 2 kDal of the macromolecule. One or more different polypeptides may be linked to the same macromolecule.

The manner of linking is conventional, employing such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The subject polypeptide may be derivatized by linking, may be linked while bound to a support, or the like.

The polypeptides of the invention may be used as reagents in assays to detect antibodies to HIV-1 or HIV-2 or antigens thereof. The polypeptides may be employed as labeled or unlabeled reagents depending upon their use. (By label is intended a molecule which provides, directly or indirectly a detectable signal.) Various labels may be employed, such as radionuclides, enzymes, fluorescers, chemiluminescers, enzyme substrates, cofactors or inhibitors, particles, e.g., magnetic particles, combinations of ligands and receptors, e.g., biotin and avidin, or the like. In addition the polypeptides may be modified in a variety of ways for binding to a surface, e.g., microwell plate, glass beads, chromatographic surface, e.g., paper, cellulose, silica gel, or the like. The particular manner which the polypeptides are joined to another compound or surface is conventional and finds ample illustration in the literature. See, for example, U.S. Pat. Nos. 4,371,515; 4,487,715; and patents cited therein.

Various assay protocols may be employed for detecting the presence of either antibodies to retroviral proteins or retroviral proteins themselves. Of particular interest is using the polypeptide as the labeled reagent, where the label allows for a detectable signal, or binding the polypeptide, either directly or indirectly to a surface, where antibody or the polypeptide in the sample will become bound to the polypeptide on the surface. The presence of human antibody bound to the polypeptide can then be detected by employing a xenogeneic antibody specific for human immunoglobulin, normally both human IgM and IgG, or a labeled protein specific for immune complexes, e.g., RF factor or S. aureus.

Various heterogeneous protocols may be employed, either competitive or non-competitive. Polypeptide may be bound to a surface or support ("support") and labeled antibody allowed to compete with antibody in the sample for the limited amount of bound polypeptide. The amount of label bound to the support would be related to the amount of competitive antibody in the sample.

Xenogeneic anti-human antibody, e.g., antibodies to the Fc of IgG and IgM (immunoglobulins), could be bound to a support. The sample would be contacted with the immunoglobulins and labeled polypeptide, whereby the amount of labeled polypeptide bound to the support would be indicative of the presence of the cognate antibodies.

Alternatively, homogeneous assays can be employed where the polypeptide is bound to an enzyme, fluorescer, or other label, where the binding of antibody to the polypeptide results in being able to discriminate between the label involved with a specific binding pair complex and label which is not involved in the complex. For assays involving such techniques, see for example U.S. Pat. Nos. 3,817,837; 3,850,752; 3,901,654; 3,935,074; 3,984,533; 3,996,345; 4,034,074; and 4,098,876, whose disclosures are incorporated herein by reference.

As an illustration of the subject invention the subject polypeptide may be conjugated to a fluorescent molecule, such as fluorescein, rhodamine or umbelliferone. In this assay the fluorescence polarization is different between complexed and uncomplexed polypeptide conjugate. Apparatuses are available for measuring changes in fluorescence polarization, e.g., TDx supplied by Abbott Laboratories, Chicago, Ill.

Illustrative of an assay technique is the use of a sample container, e.g. microwell plate wells, where the subject polypeptide or conjugates thereof are adhered to the container bottom and/or walls either covalently or noncovalently. The sample, normally human blood or serum diluted in appropriately buffered medium, is added to the container and a sufficient time allowed for complex formation between the polypeptide(s) and any cognate antibodies in the sample. The supernatant is removed and the container washed to remove nonspecifically bound proteins.

A labeled specific binding protein which specifically binds to the complex is employed for detection. To the container may be added xenogeneic antisera to human immunoglobulin, particularly anti-(human IgM and IgG) in an appropriately buffered medium. The xenogeneic antisera will normally be labeled with a detectable label, e.g., horseradish peroxidase. The label may then be detected. For example, with an enzyme, after removal of non-specifically bound enzyme label, a developer solution is added. The developer solution will contain an enzyme substrate and possibly enzyme cofactors, chromogens, etc., which, upon reaction, provide a colored, fluorescent, or chemiluminescent product which may be detected calorimetrically, fluorimetrically, or by photon counting, respectively.

The polypeptide can be prepared in a wide variety of ways. The polypeptide, because of its relatively short size, may be synthesized in solution or on a solid support in accordance with known protocols. See, for example, Stewart and Young, Solid Phase polypeptide Synthesis, $2^{nd}$ ed., Pierce Chemical Co., 1984; and Tam et al, *J. Am. Chem. Soc.* (1983) 105:6442.

Alternatively, recombinant DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. See, for example, Maniatis et al, Molecular Cloning, A Laboratory Manual, CSH, Cold Spring Harbor Laboratory, 1982. Or, the region of the viral genome coding for the polypeptide may be cloned by conventional recombinant DNA techniques and expressed (see Maniatis, supra).

Fragments from a sequence may be employed for expression of polypeptide fragments, conservative base changes can be made, where the modified codon(s) code for the same amino acid(s), or non-conservative changes in the coding sequence may be made, where the resulting amino acid may be a conservative or non-conservative change in the amino acid sequence, which was discussed previously.

The coding sequence may be extended at either the 5'- or 3'-terminus or both termini to extend the polypeptide, while retaining its epitopic site(s). The extension may provide for an arm for linking, e.g., to a label, such as an enzyme, for joining this and other polypeptides together in the same chain, for providing antigenic activity, or the like.

For expression, the coding sequence will be provided with start and stop codons, promoter and terminator regions and usually a replication system to provide an expression vector for expression in a cellular host, e.g., prokaryotic or eukaryotic, bacterial, yeast, mammal, etc.

The DNA sequence by itself, fragments thereof, or larger sequences, usually at least 15 bases, preferably at least 18 bases, may be used as probes for detection of retroviral RNA or proviral DNA. Numerous techniques are described, such as the Grunstein-Hogness technique, Southern technique, Northern technique, dot-blot, improvements thereon, as well as other methodology. See, for example, WO 83/02277 and Berent et al, *Biotechniques* (1985) 3:208.

Conveniently, the polypeptide may be prepared as a fused protein, where the polypeptide may be the N- or C-terminus of the fused polypeptide. The resulting fused protein could be used directly by itself as the reagent or the subject polypeptide may be cleaved from all or a portion of the remaining sequence of the fused protein. With a polypeptide where there are no internal methionines, by introducing a methionine at the fusion site, the polypeptide may be cleaved employing cyanogen bromide. Where there is an internal methionine, it would be necessary to provide for a proteolytic cleavage site, e.g., polylysine and/or—arginine or combinations thereof, or the internal methionine could be substituted by an amino acid such as leucine and an N-terminal methionine added for cyanogen bromide cleavage. A wide variety of proteases, including dipeptidases, are well known, and the appropriate processing signal could be introduced at the proper site. The processing signal may have tandem repeats so as to insure cleavage, since the presence of one or more extraneous amino acids will not interfere with the utility of the subject polypeptides.

Depending upon the nature of the assay, the physiological sample, e.g., saliva, blood, plasma, or serum, may be pretreated by dilution into an assay medium, which will usually be an aqueous buffered medium employing one of a variety of buffers, such as phosphate, tris, or the like. A preferred diluent is 5% w/v nonfat dry milk, 0.01% Proclin 300, 0.005% Antifoam A in 150 mM sodium citrate. Usually the pH will be in the range of about 6 to 9. The sample will then be combined with the reagent in accordance with appropriate protocol and sufficient time allowed for binding. Where a heterogeneous system is used, usually the binding stages will be followed by washes to minimize non-specific binding. At the end of the procedure, the label will be detected in accordance with conventional methods.

Besides the use of the subject polypeptide and its analogs in assays, the subject polypeptide may also find use by itself or in combination in vaccines. The polypeptides may be formulated in a convenient manner, generally at concentrations in the range of 1 ug to 20 mg/kg of host. Physiologically acceptable media may be used as carriers, such as sterile water, saline, phosphate buffered saline, and the like. Adjuvants may be employed, such as aluminum hydroxide gel, or the like. Administration may be by injection, e.g., intramuscularly, intraperitoneally, subcutaneously, intravenously, etc. Administration may be one or a plurality of times, usually at one to four week intervals.

The immunoreactivity of each of the above-mentioned polypeptides which immunologically mimic HIV-1 antigens to eight known HIV-1 positive sera (i.e. GS91-[034, 037, 042, 046, 049, 052, 056, and 067], 11230, 11424, 11527, 11532 and 11535; all Western-blot all band positives) was examined, and the results are shown in Table 1A of Example 2. All of the polypeptides listed above were highly reactive to those samples.

Analogously, the immunoreactivity of each of the above-mentioned polypeptides which immunologically mimic HIV-2 antigens to five known HIV-2 positive sera (i.e. 92099, 92100, P-83, P-84, and P-86; Western-blot all band positive) was examined, and the results are shown in Table 1B of Example 2. The glycoprotein (gp) polypeptide, 41-2-3GC (a nonglycosylated polypeptide that is the subject of co-pending U.S. application Ser. No. 08/268,388) was highly reactive to all five samples. All of the polypeptides listed above were reactive to at least two of those five samples. The most reactive polypeptides were ROD 124C2X and ROD 124C5X; they were reactive to all five samples.

EXAMPLE 1

Synthesis of HIV Pol Polypeptides

Series of HIV pol polypeptides were each synthesized by the sequential coupling of t-butyloxycarbonyl-protected amino acids onto 0.35 mmol p-methylbenzhydrylamine resin (Applied Biosystems Inc., Foster City, Calif.). Amino acid side chain protection was done by standard benzyl based groups. The tryptophan residue was protected by the formyl moiety. Completed polypeptides were deprotected and cleaved from the resin by the standard high HF procedure or the low-high HF procedure of Tam et al (J. Amer. Chem. Soc. 105:6442, 1983). The cleaved polypeptide was extracted from the resin in 50% acetic acid and subjected to Sephadex G-25 chromatography, using 20% acetic acid as a eluting solvent. Fractions containing polypeptide were pooled and lyophilized.

EXAMPLE 2

Immunoreactivity of Pol Polypeptides

Polypeptides of the invention were tested for immunological reactivity by ELISA as previously described in U.S. Pat. No. 4,629,783. Briefly, stock solutions of polypeptides of the invention at 0.5 mg/ml were prepared in 2M urea/5% acetic acid. Twelve milliters of 1.2% acetic acid was placed in a 15 milliliter polypropylene tube and 48 microliters of the polypeptide stock solution added to the tube and mixed (the "coating solution"). Wells of microwell plates were filled with 100 ul of the coating solution of the polypeptides and 100 ul/well of 0.24M carbonate/0.2N NaOH added to raise the coating solution to an alkaline pH. The plate was covered and allowed to stand overnight at room temperature. The coating solution was removed by aspiration and 300 μl/well of Plate Blocking solution (containing per liter; 25 g non-fat dry milk, 14.7 g sodium citrate dihydrate, 8.47 g sodium chloride and 0.05 ml Antifoam A, 1.0 ml Kathon GC/ICP) was added and incubated for 1 hr. at room temperature. Blocking solution was removed by aspiration, and the plates were used immediately or allowed to air-dry and stored for later use. To carry out the immunoassay, plasma samples were diluted 20-fold in Specimen Diluent (containing per liter; 44.1 g sodium citrate dihydrate, 1.2 ml Tween 20, 50 g non-fat dry milk, 0.05 ml Antifoam A, 50 ml goat serum, 58.6 g 2-[N-morpholino]ethane sulfonic acid, 92.9 g triethanolamine hydrochloride, 1 ml Proclin 300) and 100 ul was added to individual wells. Samples were incubated for 30 minutes at 37° C., then removed and the wells were washed five times with 0.1M NaCl/0.05% Tween 20 (350 μl/wash). One hundred microliters of goat antihuman Ig-horseradish peroxidase conjugate diluted in citrate buffer, pH 7.0, containing 1% normal goat serum was added to each well for 30 minutes at 37° C. prior to washing five times as above. The ELISA assay was developed by adding 100 ul/well of substrate solution (80 ug/ml tetramethylbenzidine, 0.0015% hydrogen peroxide in citrate/phosphate buffer, pH 6.0) for 30 minutes at room temperature. Reactions were stopped with the addition of 100 ul of 1N $H_2SO_4$ per well, and the ratio of the optical density at 450 nm to 630 nm was determined by an automated ELISA reader. The cut-off value for a positive result was set at 0.200 Absorbance Units above the average absorbance obtained from at least three known negative samples.

The results in Table 1A shows the reactivity of the polypeptides of the invention with HIV-1 positive and negative samples wherein the HIV-1 positive samples are GS91-(034, 037, 042, 046, 049, 052, 056, 067), 11230, 11424, 11527, 11532 and 11535, and the negative samples are PS1059–PS1062, PS1068, PS1071, and D21–D25.

TABLE 1A

| | Absorbance (450 nm/630 nm)** | | | |
|---|---|---|---|---|
| Sample* | BRU124E1 | BRU124F1X | BRU124F3X | BRU124EX*** |
| GS91-034 | 0.606 | 1.000 | 0.945 | n.d. |
| GS91-037 | 0.507 | 1.584 | 1.551 | n.d. |
| GS91-042 | 1.860 | 1.899 | 1.888 | n.d. |
| GS91-046 | 1.598 | 1.848 | 1.831 | n.d. |
| GS91-049 | 1.034 | 1.955 | 1.991 | n.d. |
| GS91-052 | 1.606 | 1.852 | 1.917 | n.d. |
| GS91-056 | 1.848 | 1.966 | 1.957 | n.d. |
| GS91-067 | 1.960 | 2.110 | 2.110 | n.d. |
| PS1071 | 0.036 | 0.040 | 0.046 | n.d. |
| PS1062 | 0.041 | 0.047 | 0.046 | n.d. |
| PS1070 | 0.034 | 0.039 | 0.043 | n.d. |
| PS1061 | 0.020 | 0.023 | 0.021 | n.d. |
| PS1069 | 0.034 | 0.039 | 0.039 | n.d. |
| PS1060 | 0.027 | 0.052 | 0.044 | n.d. |
| PS1068 | 0.028 | 0.039 | 0.037 | n.d. |
| PS1059 | 0.043 | 0.046 | 0.049 | n.d. |
| 11535 | n.d. | n.d. | n.d. | 1.652 |
| 11527 | n.d. | n.d. | n.d. | 2.595 |
| 11532 | n.d. | n.d. | n.d | 2.912 |
| 11424 | n.d. | n.d. | n.d. | 2.676 |
| 11230 | n.d. | n.d. | n.d | 0.759 |
| D21 | n.d. | n.d. | n.d. | 0.096 |
| D22 | n.d. | n.d. | n.d. | 0.045 |
| D23 | n.d. | n.d. | n.d. | 0.053 |
| D24 | n.d. | n.d. | n.d. | 0.044 |
| D25 | n.d. | n.d. | n.d | 0.034 |

*Samples were diluted 1/40, instead of 1/20, in order to be able to compare the absorbance between different polypeptides. The GS91-(034, 037, 042, 046, 049, 052, 056, 067), 11230, 11424, 11527, 11532, and 11535) are known HIV-1 positive samples; samples PS1059–PS1062, PS1068, PS1071, and D21–25 are known HIV-1 negative samples.
**Highlighted values are positive values based on the cut-off values established by 0.200 + average negative. Cut-Off = 0.238 (except BRU124EX) The Cut-Off value for BRU124EX = 0.254
***The testing for the reactivity of BRU124EX was done separately at different date, using different samples.
n.d. = not done (or tested)

The results in Table 1B show the reactivity of the polypeptides of the invention with HIV-2 positive and negative samples wherein the HIV-1 positive samples are 92099, 92100, P-83, P-84 and P-86 and the negative samples are NBD1, NBD2, NBD3, AND NBD4.

TABLE 1B

| | Absorbance (450 nm/630 nm)* | | | | | | | |
|---|---|---|---|---|---|---|---|---|
| Sample | 41-2-3GC | E1 | EX | C1X | C2X | C3X | C5X | 2A1 |
| 92099 | >3.00 | 0.41 | 0.73 | 0.24 | 1.61 | 0.78 | 1.77 | 1.91 |
| 92100 | >3.00 | 0.47 | 0.75 | 0.26 | 1.91 | 0.88 | 1.82 | 1.86 |
| P-83 | 2.82 | 0.44 | 1.05 | 0.10 | 1.02 | 0.45 | 1.06 | 0.08 |
| P-84 | >3.00 | 0.47 | 1.04 | 0.27 | 0.75 | 0.40 | 0.73 | 0.18 |
| P-86 | >3.00 | 0.16 | 0.23 | 0.16 | 0.35 | 0.20 | 0.34 | 0.13 |
| NBD1 | 0.07 | 0.06 | 0.06 | 0.05 | 0.05 | 0.05 | 0.05 | 0.09 |

TABLE 1B-continued

| | Absorbance (450 nm/630 nm)* | | | | | | | |
|---|---|---|---|---|---|---|---|---|
| Sample | 41-2-3GC | E1 | EX | C1X | C2X | C3X | C5X | 2A1 |
| NBD2 | 0.11 | 0.11 | 0.12 | 0.11 | 0.11 | 0.11 | 0.12 | 0.11 |
| NBD3 | 0.04 | 0.03 | 0.05 | 0.03 | 0.03 | 0.05 | 0.03 | 0.03 |
| NBD4 | 0.07 | 0.05 | 0.06 | 0.05 | 0.04 | 0.05 | 0.07 | 0.05 |

Highlighted values are positive values based on the cut-off values established by 0.200 + average Negative. Cut-Off = 0.256
Known positive samples are 92099, 92100, P-83, P-84 and P-86 and the known negative samples are NBD1, NBD2, NBD3, AND NBD4.

An improvement on the specificity of HIV-1 and HIV-2 antibody detection by the incorporation of pol polypeptides (BRU124F3X and ROD124C5X) is illustrated by the study results shown in Table 1 C. In this study, the pol polypeptides were coated on the microwell plate individually or together with envelope specific polypeptides, as mentioned in U.S. Pat. No. 5,439,792, the teachings of which are hereby incorporated by reference. For the plate coating with individual pol polypeptides, the polypeptide was coated at 1.0 ug/ml. For the plate coating of the mixture of HIV-1 and HIV-2 polypeptides, the polypeptides were mixed together at the following concentrations in the coating buffer: 1.23 ug/ml for HIV-1 envelope polypeptide (designated as MNGC), 0.64 ug/ml for HIV-2 envelope polypeptide (designated as 41-2-3GC), 0.25 ug/ml for BRU124F3X and 0.125 ug/ml for ROD124C5X. The polypeptide coating procedure was the same as described earlier in the "immunoreactivity" section. The samples tested are known HIV-1 (Western blot all-band positive) samples (i.e. SAL040, SAL041, SAL059, SAL063, SAL064), known HIV-2 (Western blot all-band positive) samples (i.e. 52, GB92000128, GB92000152, GB92000154, GB92000158), HIV-1 indeterminate samples (i.e. B3113, B5813, B5885, B7045, C000127, C000214, C000455) and HIV-2 indeterminate samples (i.e. B3123, B5605, B5810, B5826, B5832, B5875, B6312). Also included are the control samples used in the Genetic Systems® HIV-1/HIV-2 Peptide EIA kit (available from Sanofi Diagnostics Pasteur, Inc., Redmond, Wash.), namely HIV-1 positive control (PC-1), HIV-2 positive control (PC-2) and negative control (NC). Both the known positive and the indeterminate samples were also tested on a commercially available viral lysate based test, the Genetic Systems® HIV-1/HIV-2 EIA (Sanofi Diagnostics Pasteur, Inc., Redmond, Wash.).

Table 1C shows that all of the known HIV-1 and HIV-2 positive samples showed positive results when using either a single pol polypeptide coated plate or the plate coated with all four polypeptides. All HIV-1 and HIV-2 indeterminate samples showed negative results when using either a single pol polypeptide coated plate or the plate coated with all four polypeptides. The indeterminate samples showed highly positive results (false positive) when tested using the viral lysate-based HIV-1/HIV-2 EIA. These results very clearly show that the polypeptide based EIA incorporating the pol polypeptides of the invention, is highly sensitive and specific in detecting HIV positive samples.

It is evident form the foregoing results that by employing one or a combination of polypeptides of the subject invention, a sensitive, accurate test for the presence of antibodies to HIV is provided. The subject polypeptides can be used by themselves or in combination with a screening assay or confirmatory assay, whereas the complete lysate or complete antigens may be employed as an independent procedure. The subject polypeptides can also be combined with polypeptides or proteins derived from the envelope or gag regions of HIV-1 or HIV-2 in a screening assay or confirmatory assay. Furthermore, because of the specificities of the polypeptides, one could anticipate that the DNA sequences coding for the polypeptides would also find similar specificity in a DNA hybridization assay.

The invention now being fully described, it will be apparent to one of ordinary skill in the art that many changes and modifications can be made thereto without departing from the spirit or scope of the appended claims.

What is claimed is:

1. A method for determining the presence of antibodies to HIV in a body fluid, comprising:
   (a) providing a body fluid;
   (b) contacting, under conditions which permit immunospecific binding to form a reaction mixture, the body fluid with a composition containing at least one polypeptide of no more than 60 amino acid residues in length and having the following polypeptide sequence:
   (III) BRU124F1X (SEQ ID NO: 3)
   W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Val-Val-Ile-Gln-Asp-Asn-Ser-Asp-Ile-Lys-Y-Z
   wherein W is either a H of the amino terminal NH$_2$ group of the polypeptide or an additional amino acid bonded to the amino terminal NH$_2$ group of the polypeptide, the additional amino acid being selected to facilitate coupling of the polypeptide to a carrier protein or to a support; X is absent or Cys-Gly-Gly; Y is absent or Cys; and Z is OH or NH$_2$; and
   (c) detecting whether immunospecific binding has occurred between the polypeptide and an antibody component of the body fluid in which an immune complex is formed and in which the detection of the immune complex indicates the presence of antibodies to HIV in the body fluid.

2. The method according to claim 1 in which the polypeptide is conjugated to a carrier macromolecule.

3. The method according to claim 1 in which the polypeptide is immobilized.

4. The method according to claim 1 in which the immunospecific binding is detected by immunoprecipitation.

5. The method according to claim 1 in which the composition includes at least one polypeptide selected from a polymerase protein of HIV-1 and one selected from a polymerase protein of HIV-2.

6. The method according to claim 1 in which immunospecific binding between the polypeptide or protein and the antibody component of the body fluid is detected by:
   (i) removing unbound components from immune complexes formed in the immunoreaction mixture;
   (ii) adding a labeled antibody to the immunoreaction mixture, the labeled antibody being capable of immunospecifically binding to a component of the immune complexes and the label providing a detectable signal; and
   (iii) determining whether the labeled antibody binds to the immune complexes.

7. The method according to claim 6 in which the label comprises an enzyme which is detected by the addition of the enzyme substrate.

8. The method according to claim 6 in which the label comprises a radiolabel.

9. The method according to claim 6 in which the label comprises a fluorescent label.

10. A method for determining the presence of antibodies to HIV-1 in a body fluid, comprising:
    (a) providing a body fluid;
    (b) contacting, under conditions which permit immunospecific binding to form a reaction mixture, the body fluid with a composition containing at least one polypeptide of no more than 60 amino acid residues in length and having the following polypeptide sequence:
    (III) BRU124FX1 (SEQ ID NO: 3)
    W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Val-Val-Ile-Gln-Asp-Asn-Ser-Asp-Ile-Lys-Y-Z wherein W is either a H of the amino terminal NH$_2$ group of the polypeptide or an additional amino acid bonded to the amino terminal NH$_2$ group of the polypeptide, the additional amino acid being selected to facilitate coupling of the polypeptide to a carrier protein or to a support; X is absent or Cys-Gly-Gly; Y is absent or Cys; and Z is OH or NH$_2$; and (c) detecting whether immunospecific binding has occurred between the polypeptide and an antibody component of the body fluid in which an immune complex is formed and in which the detection of the immune complex indicates the presence of antibodies to HIV in the body fluid.

11. A method for determining the presence of antibodies to HIV in a body fluid, comprising:

(a) contacting, under conditions which permit immunospecific binding to form a reaction mixture, the body fluid with a composition containing a combination of HIV-1 and HIV-2 envelope and polymerase polypeptides, said combination comprising (i) at least one HIV-1 envelope polypeptide;

(ii) at least one HIV-2 envelope polypeptide;

(iii) at least one HIV-1 polymerase polypeptide having the following polypeptide sequence:

(III) BRU124F1X (SEQ ID NO: 3)

W-X-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-Val-Val-Ile-Gln-Asp-Asn-Ser-Asp-Ile-Lys-Y-Z and (iv) at least one HIV-2 polymerase polypeptide having a polypeptide sequence selected from the group consisting of:

(V) ROD 124E1 (SEQ ID NO: 5)

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Y-Z (VI) ROD 124EX (SEQ ID NO: 6)

W-X-Leu-Gln-Ala-Lys-Asn-Ser-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Y-Z (VII) ROD 124C2X (SEQ ID NO: 7)

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Y-Z (VIII) ROD 124C1X (SEQ ID NO: 8)

W-X-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Y-Z (IX) ROD 123C3X (SEQ ID NO: 9)

X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Y-Z (X) POL2A1 (SEQ ID NO: 10)

W-X-Lys-Gly-Pro-Gly-Glu-Leu-Leu-Trp-Lys-Gly-Glu-Gly-Ala-Val-Leu-Val-Lys-Val-Gly-Thr-Asp-Ile-Lys-Ile-Ile-Pro-Arg-Arg-Lys-Ala-Lys-Ile-Ile-Y-Z (XI) ROD124C5X (SEQ ID NO: 11)

W-X-Lys-Leu-Lys-Asp-Phe-Arg-Val-Tyr-Phe-Arg-Glu-Gly-Arg-Asp-Gln-Leu-Trp-Lys-Gly-Pro-Gly-Glu-Leu-Leu-Trp-Lys-Gly-Glu-Gly-Ala-Val-Leu-Val-Lys-Val-Gly-Y-Z wherein W is either a H of the amino terminal NH$_2$ group of the polypeptide or an additional amino acid bonded to the amino terminal NH$_2$ group of the polypeptide, the additional amino acid being selected to facilitate coupling of the polypeptide to a carrier protein or to a support; X is absent or Cys-Gly-Gly; Y is absent or Cys; and Z is OH or NH$_2$; and (b) detecting whether immunospecific binding has occurred between the polypeptide and an antibody component of the body fluid in which an immune complex is formed and in which the detection of the immune complex indicates the presence of antibodies to HIV in the body fluid.

* * * * *